United States Patent [19]
Burkett

[11] Patent Number: 4,836,752
[45] Date of Patent: Jun. 6, 1989

[54] PARTIAL RESTRICTION DETECTOR

[75] Inventor: David Burkett, San Diego, Calif.

[73] Assignee: Fisher Scientific Company, Pittsburgh, Pa.

[21] Appl. No.: 115,702

[22] Filed: Nov. 2, 1987

[51] Int. Cl.$^4$ .................. F04B 43/12; F04B 49/00
[52] U.S. Cl. ........................... 417/12; 417/38; 417/63; 417/474; 417/479; 604/152; 604/153; 604/67
[58] Field of Search ............... 417/12, 38, 53, 63, 417/474, 478, 479; 604/67, 118, 151–153

[56] References Cited

U.S. PATENT DOCUMENTS

| | | | |
|---|---|---|---|
| 3,424,883 | 1/1969 | Heskett | 417/38 |
| 3,985,133 | 10/1976 | Jenkens et al. | 604/152 X |
| 4,244,365 | 1/1981 | McGill et al. | 604/118 |
| 4,277,226 | 7/1981 | Archibald | 417/63 X |
| 4,277,227 | 7/1981 | Jenkins | 417/63 |
| 4,369,780 | 1/1983 | Sakai | 417/38 X |
| 4,373,525 | 2/1983 | Kobayashi | 417/63 X |
| 4,391,599 | 7/1983 | Jenkins | 604/152 X |
| 4,394,862 | 7/1983 | Shim | 604/67 |
| 4,444,546 | 4/1984 | Pazemenas | 417/12 |
| 4,526,574 | 7/1985 | Pekkarinen | 604/118 X |
| 4,530,696 | 7/1985 | Bisera et al. | 604/67 X |
| 4,563,179 | 1/1986 | Sakai | 417/38 X |
| 4,617,014 | 10/1986 | Cannon et al. | 604/67 |
| 4,690,673 | 9/1987 | Bloomquist | 604/67 |
| 4,702,675 | 10/1987 | Aldrovandi et al. | 417/63 |

Primary Examiner—Carlton R. Croyle
Assistant Examiner—Eugene L. Szczecina, Jr.
Attorney, Agent, or Firm—Nydegger & Harshman

[57] ABSTRACT

A device for detecting partial restriction in a fluid line connecting a fluid source with an IV infusion pump comprises a gauge mounted on the pump and operatively associated with the line to determine fluid pressure therein. The pump also comprises a peristable finger to conditionally occlude the line and a miroprocessor, upon occlusion of the line, to establish fluid pressure parameters within which the indication is that there is no partial restriction in the line. The pump also uses the microprocessor to compare actual pressure measured by the gauge during an occlusion with the established parameters to determine whether pump operation is to be continued.

16 Claims, 5 Drawing Sheets

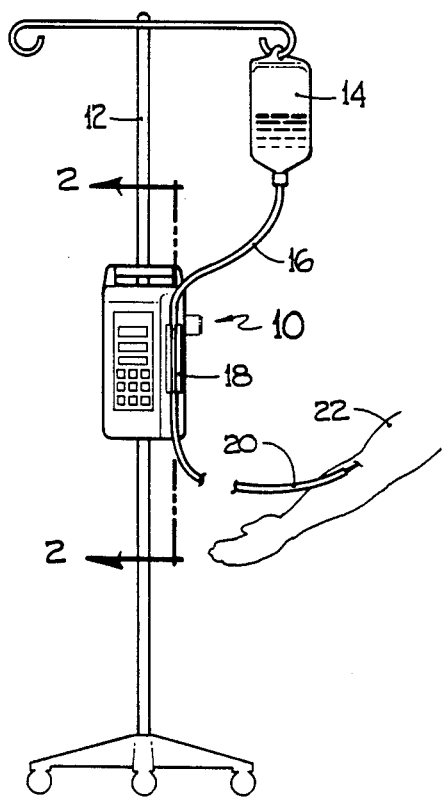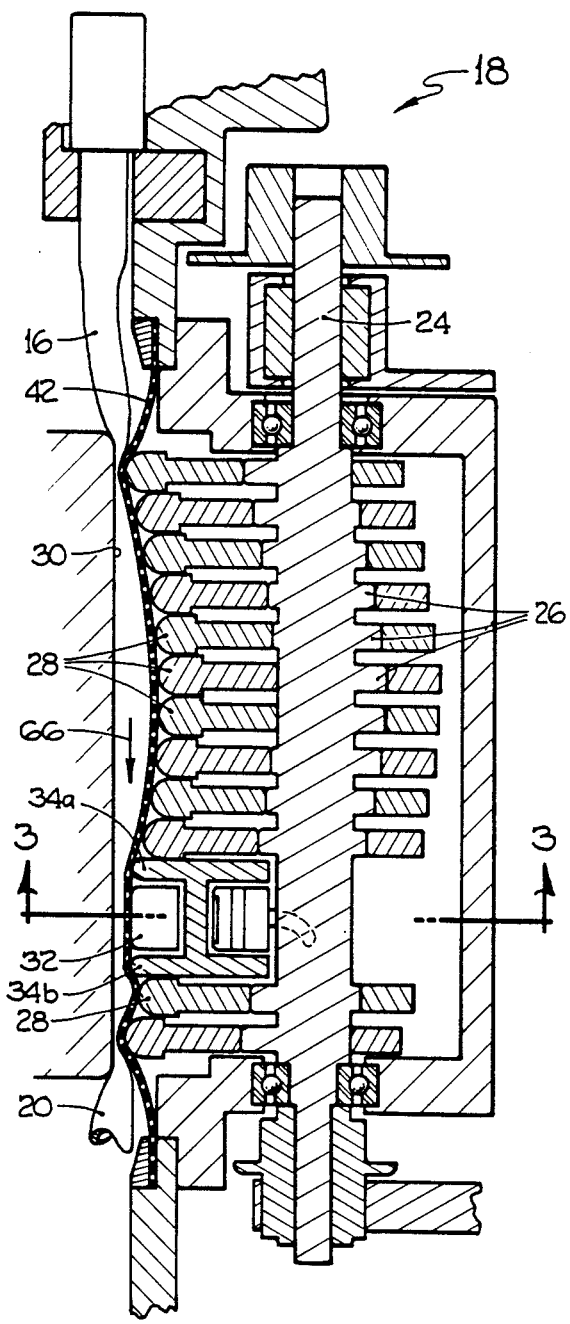

PARTIAL RESTRICTION DETECTOR

BACKGROUND OF THE INVENTION

This invention relates generally to devices which are useful for monitoring fluid pressure in a fluid line and indicating when variations in pressure exceed established limits. More particularly, the present invention relates to a device which monitors fluid flow through a resilient tube to detect when there is a partial restriction to fluid flow through the tube. The present invention is particularly, but not exclusively, useful in the health care field in combination with an IV infusion pump for the administration of medical solutions to a patient.

DESCRIPTION OF THE PRIOR ART

As is well known in the health care field, unwanted restrictions or occlusions in the fluid line of an IV administration system can have serious consequences for the patient to which medical solutions are being administered. Accordingly, much effort has been given to detecting such conditions before complications result. It is known that the incorporation of a fluid pump in an IV administration system will help alleviate problems caused by fluid line restrictions. Use of a pump, however, does not completely solve these problems. Indeed, it can even create other problems. The conclusion is that partial restrictions in a fluid line cannot be ignored.

Previously, the concern with IV administration systems incorporating pumps has focused on identifying excessive fluid pressures in the system which would indicate the presence of an occlusion. For example, U.S. Pat. No. 4,244,365 to McGill et al. discloses an overpressure device useful for this purpose. Also, U.S. Pat. No. 4,277,227 to Jenkins discloses a device which is activated to indicate a restriction or occlusion whenever a predetermined fluid pressure is attained. On the other hand, devices such as the one disclosed in U.S. Pat. No. 4,277,226 to Archibald, react to the absence of fluid pressure in the line to indicate an occlusion. Of the many devices disclosed for actually measuring the fluid pressure in the line, a resilient diaphragm as disclosed in the '227 patent to Jenkins is typical. Another method for measuring fluid pressure is disclosed in U.S. Pat. No. 4,373,525 to Kobayashi which uses a device that measures dimensional variations in the outside diameter of a resilient tube and correlates these variations to changes in fluid pressure.

In none of these earlier references, however, has there been a teaching or suggestion that response parameters for dimensional variations in the outside diameter of a resilient fluid line can be periodically established during a downstream occlusion and that subsequent variations can be tested for compliance with these parameters. In accordance with the present invention, compliance with the established parameters indicates that normal operation can continue. On the other hand, violation of the parameters indicates the presence of a partial restriction in the upstream line.

Detection of a partial upstream restriction is important because, for one thing, the operation of a pump in a system with such a restriction can result in fluid volume errors. This is particularly so when peristaltic pumps are employed. Also, partial restrictions in the fluid line can cause resistive forces that reduce the system's overall efficiency. For example, overcoming these resistive forces can cause the pump's motor to labor. Additionally, partial restrictions in a fluid line can create disruptive fluid flow conditions within the system which cause still further problems.

The present invention recognizes that partial restrictions in the line upstream from a pump can be detected and that such detection will obviate unwanted consequences of a partial restriction. Specifically, the present invention recognizes that, for IV administration systems incorporating peristaltic pumps, fluid volume errors can result from the partial collapse of the fluid line caused when the pump attempts to pull fluid through a restriction.

Accordingly, it is an object of the present invention to provide a device for detecting partial restrictions in a fluid line. It is another object of the present invention to provide means for establishing acceptable fluid pressure parameters in the line, within which normal operation of the pump can continue. Still another object of the present invention is to provide a partial restriction detector which is relatively easy to manufacture, which is reliable and which is cost effective.

SUMMARY OF THE INVENTION

The preferred embodiment of the device for the present invention which is used to detect partial restrictions in the resilient fluid line connecting a fluid source with a pump comprises a gauge mounted on the pump for operative association with the fluid line. Specifically, the gauge is positioned to rest against the fluid line to measure dimensional variations in its outside diameter. Further, means associated with the guage correlates these dimensional variations with changes in the fluid pressure in the line. The preferred embodiment also comprises means to conditionally occlude the line downstream from the gauge and subsequently monitor the pressure variations at the location of the gauge prior to fluid pressure stabilization. The device of the present invention also comprises means to establish a threshold pressure relative to the fluid pressure immediately following the occlusion of the line and to subsequently establish a retest pressure relative to the stabilized pressure. Means are also provided to alarm the device whenever the threshold pressure is attained and to establish a new threshold pressure if the retest pressure is realized.

The present invention may be used in combination with either a peristaltic pump, in which a moving zone of occlusion is generated along the fluid line, or in combination with a valved pump, in which the valve periodically occludes the upstream line while fluid is pumped into the downstream line. Where a peristaltic pump is used, the present invention further comprises means to stop the pump for a predetermined interval of time when the occlusion is downstream from the gauge. Additionally, means are provided to extend this interval an operationally permissible increment of time in the event the fluid pressure in the line has not stabilized below the threshold pressure within the originally established interval.

The novel features of this invention as well as the invention itself, both as to its organization and operation, will be best understood from the accompanying drawings taken in conjunction with the accompanying description in which similar reference characters refer to similar parts and which:

BRIEF DESCRIPTION OF THE DRAWINGS

FIG. 1 is a front elevational view of an IV system incorporating the present invention;

FIG. 2 is a cross-sectional view of a pumping mechanism incorporating the present invention as seen along the line 2—2 in FIG. 1;

DESCRIPTION OF THE PREFERRED EMBODIMENT

Figure 3:
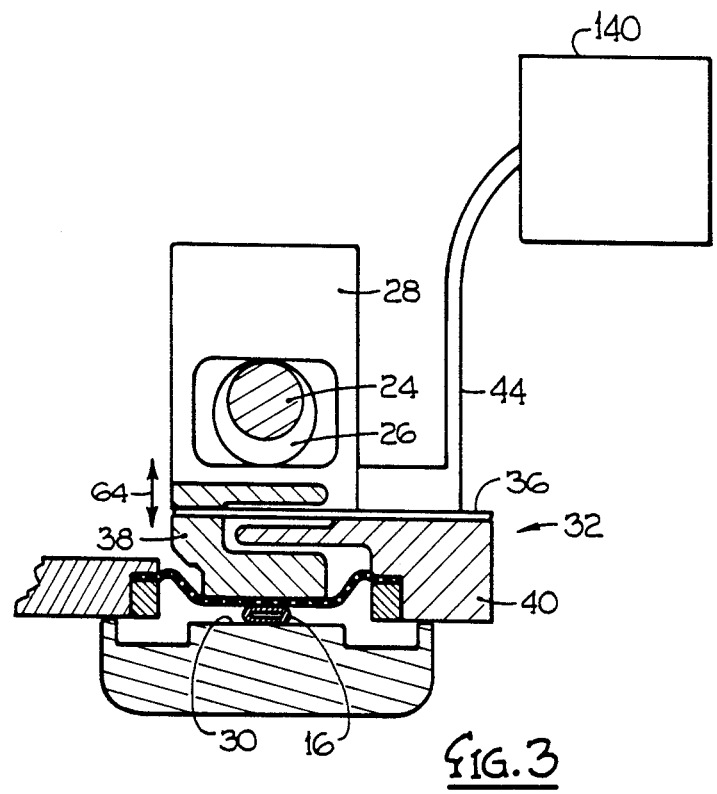
FIG. 3 is a cross-sectional view of the gauge of the present invention as presented in FIG. 1 when viewed along the line 3—3 in FIG 2.

FIG. 1 shows an IV adminstration system in which an IV pump, generally designated 10, is used. It is to be understood at the outset that, while the present invention is primarily intended for use with a peristaltic pump, it may also be used in combination with other types of pumps. As seen in FIG. 1, the pump 10 is a linear peristaltic pump and is mounted on a pole 12 on which a fluid source 14 is also hung. In accordance with standard set-up procedures, fluid source 14 is connected in fluid communication with an upstream IV tube or line 16 which is operatively associated with the pumping mechanism 18 of pump 10. A fluid line 20, downstream from pumping mechanism 18, provides for an extension of line 16 and is connected to the patient 22 in any manner well known in the pertinent art that will allow for the infusion of fluids or medical solutions to the patient 22.

Referring now to FIG. 2, it will be seen that pumping mechanism 18 is a finger-type linear peristaltic pump. Specifically, as primarily intended for the present invention, mechanism 18 has a structure and a cooperation of structure similar to the device disclosed in U.S. Pat. Nos. 4,617,014 to Cannon et al. and 4,690,673 to Bloomquist, both of which are presently assigned to the same assignee as the present invention. Briefly, FIG. 2 shows that rotation of camshaft 24 and the consequent rotation of cams 26 mounted on shaft 24 cause fingers 28 to sequentially urge against line 16 to create a moving zone of occlusion along the line 16. More specifically, fingers 28 squeeze line 16 between fingers 28 and platen 30 to create the moving zone of occlusion.

Also shown in FIG. 2, as part of mechanism 18, is a gauge 32 which is flanked by stationary fingers 34a and 34b. Although gauge 32 and stationary fingers 34a and 34b can be fully appreciated by reference to U.S. Pat. Nos. 4,617,014 to Cannon et al. or 4,690,673 to Bloomquist, the functioning of gauge 32 can also be appreciated by reference to FIG. 3. In FIG. 3 it is seen that gauge 32 comprises a flexible beam 36 on which a strain gauge (not shown) can be placed in any manner well known in the pertinent art. As will be understood by the skilled artisan, flexures of beam 36 can be converted into charges of electrical current by the strain gauge to indicate the amount of bending undergone by beam 36. FIG. 3 also shows that one end of beam 36 is connected to a pressure plate 38 while the other end of beam 36 is fixedly mounted on a base 40. Importantly, pressure plate 38 rests against line 16 with line 16 disposed between pressure plate 38 and platen 30. Consequently, since base 40 is fixed in position relative to platen 30, variations in fluid pressure in line 16 which cause the line 16 to expand or collapse between plate 38 and platen 30 will result in movement of plate 38 in the directions indicated by arrow 64. As will be known by the skilled artisan, this movement of plate 38 results in flexures of beam 36. As implied above, these flexures correlate to variations in fluid pressure within line 16. Also, these flexures cause the strain gauge (not shown) on beam 36 to generate electrical signals which are transmitted via electrical connectors 44 to a microprocessor 140 for purposes to be subsequently disclosed.

Figure 4:
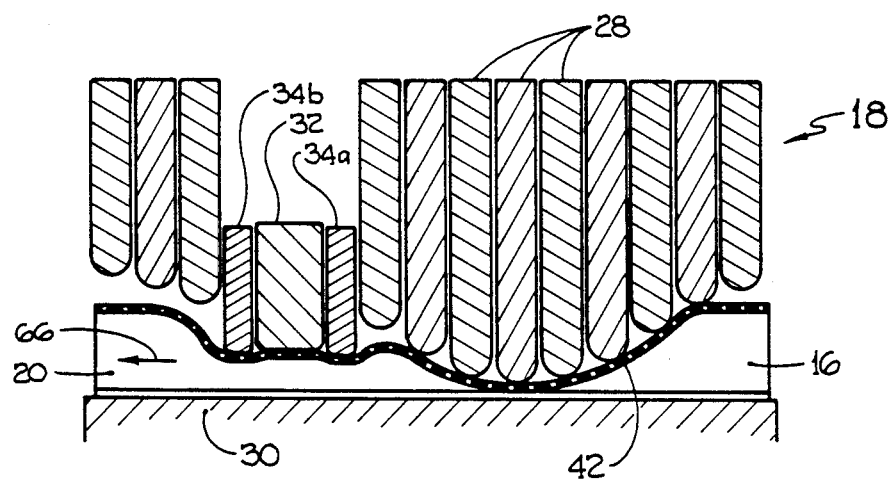
FIG. 4 is a cross-sectional view of a portion of the peristaltic mechanism shown in FIG. 2 with the peristaltic occlusion upstream from the gauge.

FIG. 4 shows gauge 32 in cooperation with the fingers 28 of mechanism 18 in a condition where an occlusion 42 is created on line 16 upstream from the gauge 32 by the interaction of finger 28 squeezing line 16 against platen 30. In this instance, and for the conditions depicted in FIGS. 5A and 5B, arrow 66 indicates the direction of operational fluid flow through line 16.

Figure 5A:
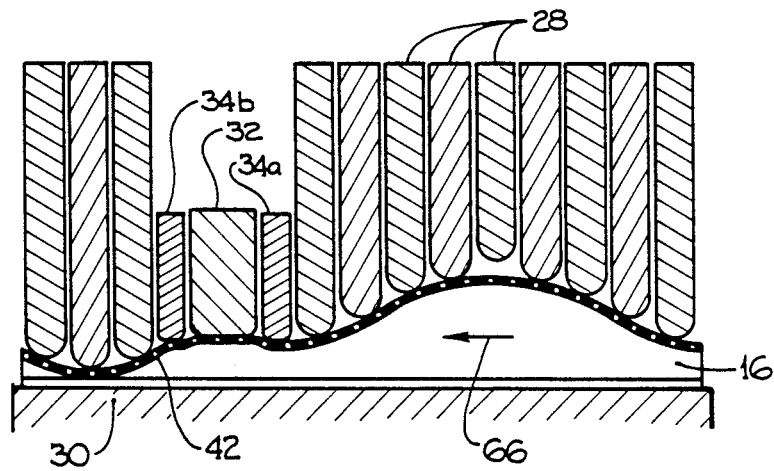
FIGS. 5A and 5B are cross-sectional views of the peristaltic mechanism shown in FIG. 4 with the peristaltic occlusion downstream from the gauge and respectively showing the results of a partially restricted tube and an unrestricted tube.
Figure 5B:
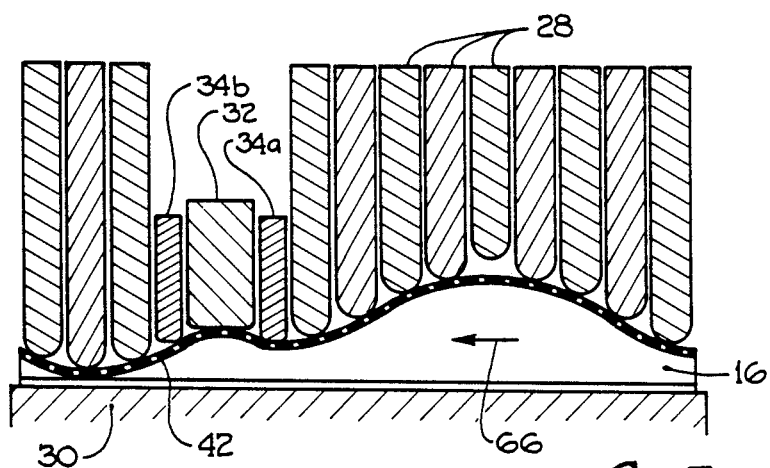

In FIGS. 5A and 5B, two different conditions are shown which can occur when the occlusion 42 is downstream from gauge 32. More specifically, FIG. 5A shows the condition wherein line 16 is reacting to a partial restriction in line 16 upstream from gauge 32. The condition in FIG. 5A will typically result immediately upon stopping operation of pump 10 when the occlusion 42 is downstream from gauge 32. This is so because line 16 has partially collapsed as a result of the attempt by pump 10 to pull fluid through a partially restricted line 16. This condition, however, is transitory. The fluid pressure in line 16 caused by the height of fluid source 14 above mechanism 18 (i.e. "bottle height") will cause line 16 to reactively expand and stabilize in a position as shown in FIG. 5B.

When there is no partial restriction in line 16, the configuration of line 16 at the time pump 10 is stopped with occlusion 42 downstream from gauge 32, will be very close to the stabilized position shown in FIG. 5B. Indeed, because line 16 is not collapsed, under this condition, the dimensional variation in line 16 required to obtain a stabilized configuration is minimal. This is of no concern. On the other hand, a variation such as shown by the transition in configuration of line 16 from that as shown in FIG. 5A to that shown in 5B is of concern. As will be subsequently discussed in greater detail, both the magnitude of this variation and the time required for eventual stabilization are important.

Figure 6:
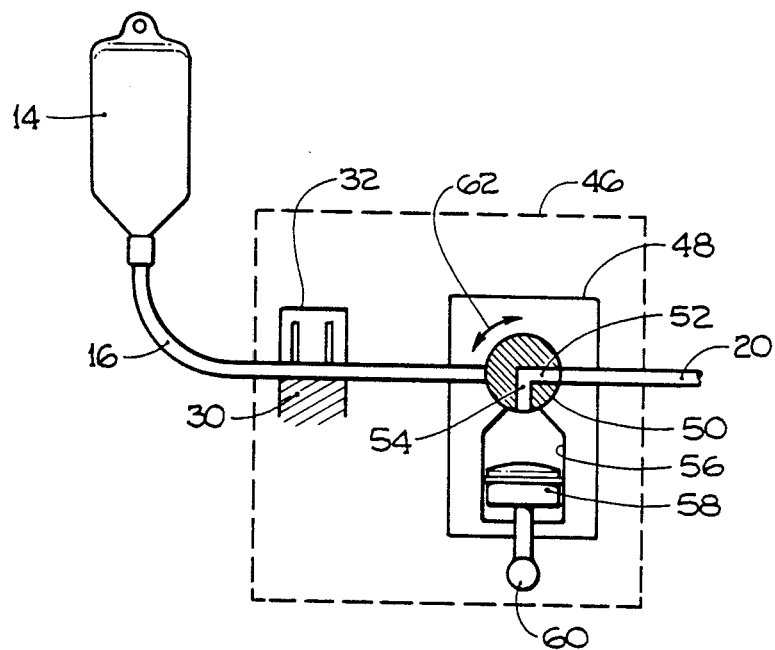
FIG. 6 is a schematic diagram of the present invention in combination with a valved pump.

In an alternate embodiment of the present invention, a gauge 32 and its associated circuitry may be used with a valved pump such as is disclosed in U.S. Pat. No. 3,985,133 to Jenkins. A pump of this type is schematically shown in FIG. 6 and is generally designated 46. Typically, a pump of this type associates with a cassette 48 which incorporates a rotatable valve 50. As shown, valve 50 has a passageway 52 intersecting a passageway 54 through which fluid can pass. According to the orientation of valve 50, fluid can be drawn into pumping chamber 56 from line 16 through valve 50 or expelled from chamber 56 and into line 20 through valve 50. Orientation of valve 50 for these purposes is established through a connection (not shown) between valve 50 and pump 46 which moves valve 50 in the direction indicated by arrow 62. The resultant movement of valve 50 is done in concert with the movement of piston 58 into and out of chamber 56. Like valve 50, piston 58 is moved by the action of pump 46. This particular action, however, is accomplished through connector 60. As will be appreciated by the skilled artisan, whenever pump 46 is pumping fluid from chamber 56 into line 20, valve 50 has occluded line 16. This resultant occlusion is effective for purposes of the present invention and, accordingly, serves the same purpose served by occlusion 42 generated by linear peristaltic pump 10. Unlike the situation with peristaltic pumping mechanism 18, however, when a valved pump 46 is used there is no need to stop pump 46 during the monitoring interval to be discussed. In all other respects, the operation of the present invention is similar regardless whether a peristaltic or a valved pump is used.

OPERATION

Figures 7A, 7B, 7C:
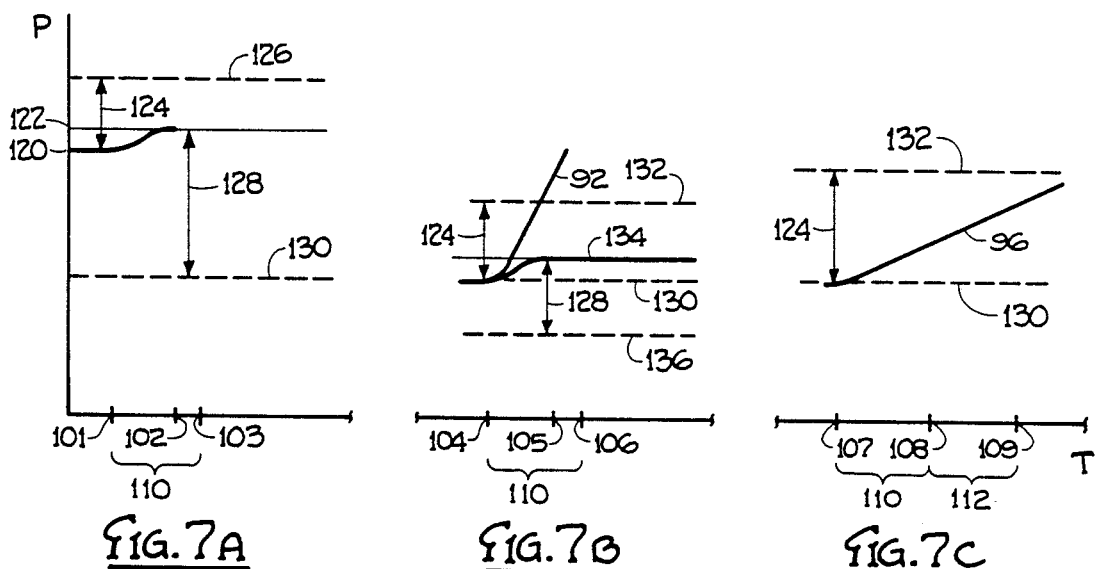
FIGS. 7A, B and C are graphic plots of pressure-time variations for upstream fluid presssure under various operating conditions.

Operation of the present invention is best understood conceptually by reference to FIGS. 7A, B and C, each of which is a graphic plot of pressure (P) versus time (T). Specifically, each figure represents an observable pressure variation in fluid line 16 as sensed by pressure sensor 32 under differing conditions. FIG. 7A shows an expected pressure variation 90 immediately after operation of pump 10 has been stopped under normal operating conditions. FIGS. 7B and 7C respectively show different pressure variations 92 and 96 which can result when there is a partial restriction in fluid line 16 upstream from the occlusion 42. In the case depicted in FIG. 7B, an upstream partial restriction collapses line 16 to a point where its expansion during rebound to stabilization traverses a greater range than would be normally expected. Again, compare FIG. 5A with 5B. In the case depicted in FIG. 7C, an upstream restriction retards expansion of line 16 to an extent where line 16 cannot effectively recover to stabilization within an acceptable time period. In either case, something must be corrected before there can be normal operation. Fortunately, each of these two cases exhibit identifiable deviations from the norm which can be detected.

First, however, the norm must be defined. How this is done will be best appreciated with reference to FIG. 7A which shows an expected pressure variation 90 at the location of sensor 32 when pump 10 is stopped and peristaltic occlusion 42 is downstream from sensor 32. Recall pressure variation 90 occurs when there is no upstream partial restriction. FIG. 7A also shows the established parameters for proper functioning of the present invention. Combining the typical pressure variations and operational parameters on a single figure is instructive since the present invention recognizes that a partial upstream restriction can be detected by observing deviations from the expected norm relative to the established acceptable operational parameters. As shown in FIG. 7A, if the peristaltic occlusion 42 is downstream from sensor 32 and the operation of pump 10 is then stopped at time 101, sensor 32 will indicate an initial pressure 120 in line 16. While pump 10 remains stopped during the interval from time 101 to time 103, "bottle height" fluid pressure in line 16 will cause line 16 to expand. This expansion results in pressure variation 90 which shows that the outer diameter of line 16 eventually stabilizes under the bottle height pressure to indicate a stabilized pressure 122. Thus, with no restrictions in line 16 upstream from occlusion 42 a pressure variation 90 between pressure 120 and pressure 122 is expected in the time interval immediately after pump 10 is stopped.

Figure 8:
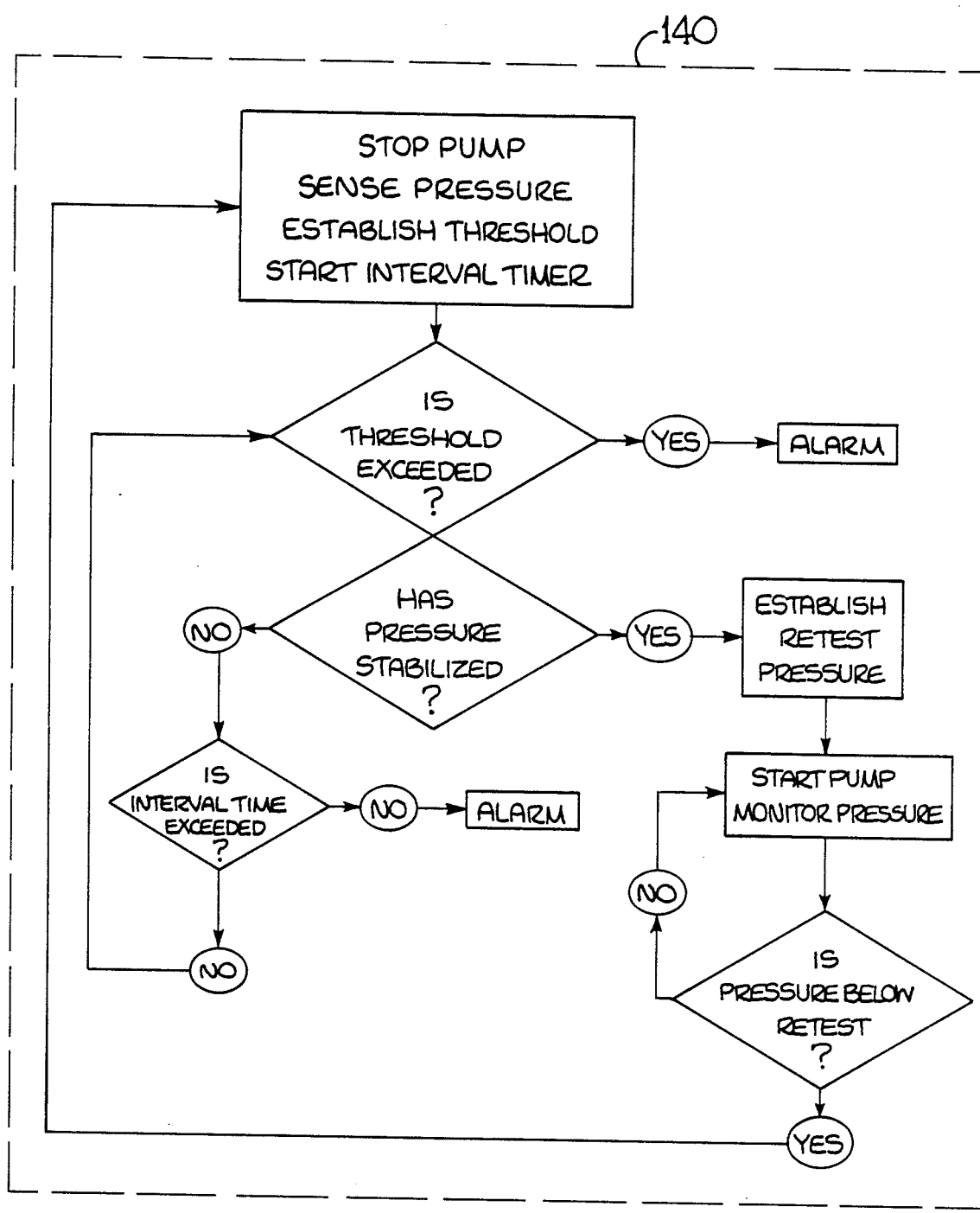
FIG. 8 is a schematic diagram of the logic flow chart indicating the organized stops accomplished by the microprocessor of the present invention.

The present invention uses this expectation to advantage by establishing pressure and time parameters within which pump 10 can continue operation. Just how this is accomplished will be best understood by considering the time sequence of events while cross-referencing FIG. 7A, FIG. 7B and FIG. 7C with FIG. 8. Start by considering that pump 10 is functionally operating under normal conditions to pump fluid through line 16. At time 101, when occlusion 42 is downstream from sensor 32, pump 10 is stopped. Simultaneous with the stopping of pump 10, line 16 senses pressure 120 and sensor 32 transfers this information to a microprocessor 140 where a pressure differential 124 is added to pressure 120 to establish threshold pressure 126. It will be understood that the microprocessor 140 used for this purpose can be of any commercially available model well known in the pertinent art. After time 101, line 16 recovers from the pumping operation and expands until it stabilizes at time 102 under the normal bottle height pressure 122. Once the fluid pressure in line 16 stabilizes at pressure 122, the microprocessor 140 uses a predetermined pressure differential 128 to establish a retest pressure 130. At time 103 pump 10 resumes its pumping operation.

As described, operation parameters are established with reference to expected pressure variation 90 during the predetermined interval 110, between time 101 and time 103, when pump 10 is stopped. Threshold pressure 126 is established at time 101 relative to initial pressure 120 and retest pressure 130 is established relative to the stabilized pressure 122. Subsequently, any pressure detected above threshold pressure 126 prior to time 103 will be used as a signal by the microprocessor 140 to alarm and cease operation of pump 10. Also, any pressure detected below retest pressure 130 will be used as a signal by the microprocessor 140 to momentarily stop pump 10 for an interval 110 and test for deviations from the expected pressure variation 90.

FIG. 7B depicts two scenarios wherein the fluid pressure in line 16 has fallen to the retest pressure 130 at a time 104. In accordance with the logic of the present invention, whenever pressure has fallen to retest pressure 130, pump 10 will be stopped for the predetermined time interval 110. In this instance, pump 10 is stopped at time 104 and predetermined pressure differential 124 is added to retest pressure 130 to establish a new threshold pressure 132. In the particular scenario for pressure variation 94, new threshold pressure 132 is not exceeded. Instead, pressure variation 94 stabilizes at time 105 at a pressure 134 within interval 110, i.e. before time 106. Pressure variation 94, closely resembles pressure variation 90. It, however, has different values. Also, within interval 110, pressure differential 128 is used by microprocessor 140 to establish a new retest pressure 136. Once all this is done, pump 10 will resume normal operation. The logic consideration in the case of pressure variation 94 is that tube 16 has merely relaxed. Accordingly, its memory has been diminished. In all other respects it behaves normally. On the other hand, if there is a partial restriction in line 16, the above scenario for pressure variation 94 will not occur. Instead, during interval 110, between time 104 and time 106, a pressure variation 92 will be monitored. With pressure variation 92, threshold pressure 132 is exceeded at time 105 within time interval 110. This indicates a partial upstream restriction in line 16 for which pump 10 can be properly programmed to alarm or cease operation.

FIG. 7C depicts yet another scenario in which the variation of fluid pressure in line 16 indicates a partial upstream restriction. In this case, fluid pressure in tube 16 has fallen to retest pressure 130 at time 107. As intended for the retest procedure, pump 10 is stopped and the predetermined time interval 110 is established from time 107 to time 108. In this scenario, however, pressure variation 96 does not exceed threshold pressure 132 established by the pressure differential 124 and does not stabilize prior to the end of interval 110. Instead, at time 108 pressure variation 96 indicates that line 16 is still expanding toward stabilization under the bottle height pressure and that threshold pressure 132 has not been attained. When this happens, the microprocessor 140 is programmed to provide for an extension of interval 110 by a period of time 112. During this extended period 112 the microprocessor 140 continues to monitor for a pressure stabilization. If, prior to time 109, pressure variation 94 has either failed to stabilize, or has attained threshold pressure 132, the microprocessor 140 will cause pump 10 to alarm or cease operation.

While the particular device for detecting partial restrictions in a fluid line as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A device for detecting a partial restriction in a fluid line connecting a fluid source in fluid communication with a pump which comprises:
   means to stop said pump for a predetermined time interval;
   means for creating an occlusion of said tube;
   a gauge operatively associated with said tube for determining fluid pressure changes in said tube upstream from the occlusion during said time interval;
   means to establish a threshold for said pressure change; and
   means for alarming when said pressure change traverses said threshold.

2. A device as cited in claim 1 wherein said gauge measures variations in the outside diameter of said tube and said device further comprises means to correlate said diameter variations with said pressure changes.

3. A device as recited in claim 2 wherein said pump is a finger peristaltic pump and said means for creating said occlusion is a peristaltic finger of said pump.

4. A device as recited in claim 3 further comprising means to define a portion of said limit as a threshold pressure value simultaneously with stopping said pump.

5. A device as recited in claim 4 further comprising means to initiate said time interval whenever the outside diameter of said line collapses to a predetermined value.

6. A device as recited in claim 5 further comprising:
   means associated with said pump to extend said time interval a determinable period when the outside diameter of said tube is expanding below the threshold value at the end of said interval; and
   means to alarm and indicate a restriction in said line when the outside diameter of said line is still expanding below the threshold level at the end of the extended time interval.

7. A device as recited in claim 2 wherein said means for creating said occlusion is a valve disposed in said fluid line, said valve being operatively connected to said pump to alternatingly open and close said tube for fluid communication with said pump.

8. A device as recited in claim 7 wherein said established time interval is initiated simultaneoulsy with closing said valve to fluid communication with said pump.

9. A device as recited in claim 8 further comprising means to define a portion of said limit as a threshold pressure value simultaneously with operation of said valve to close said tube.

10. A device for detecting restrictions in a resilient fluid line connecting a fluid source with a peristaltic pump having means to create a moving zone of occlusion along a portion of the line which comprises:
    means operatively associated with said fluid line upstream from the occlusion to determine dimensional variations in the outside diameter of said line;
    means to stop operation of said pump for a determinable time interval; and
    means to alarm and indicate a restriction in said line when the outside diameter of said line attains a predetermined threshold value during said time interval.

11. A device as cited in claim 10 further comprising means to establish said threshold value simultaneously with stopping operation of said pump.

12. A device as cited in claim 11 further comprising means to initiate said time interval whenever the outside diameter of said line collapses to a predetermined value.

13. A device as cited in claim 12 further comprising:
    means associated with said pump to extend said time interval a determinable period when the outside diameter of said tube is expanding below the threshold value at the end of said interval; and
    means to alarm and indicate a restriction in said line when the outside diameter of said line is still expanding below the threshold level at the end of the extended time interval.

14. A method for using a gauge to detect a partial restriction in a fluid line connecting a fluid source in fluid communication with a pump which comprises of the steps of:
    (a) Stopping the pump;
    (b) Occluding the line downstream from the gauge;
    (c) Measuring variations in the outside diameter of the line at a location upstream from the occlusion while the pump is stopped;
    (d) Establishing a limit value for said measured variations;
    (e) Determining whether the variation traverses said predetermined limit value; and
    (f) Alarming to indicate a partial restriction whenever the limit is traversed.

15. A method as cited in claim 14 further comprising the steps of:
    (a) Establishing the limit value simultaneously with stopping the pump; and
    (b) Waiting for an established interval of time to determine whether the variation traverses the limit.

16. A method as cited in claim 15 further comprising the step of monitoring the variations to occlude the line whenever the line collapses below a preset dimension.

* * * * *